(12) United States Patent
Kalem

(10) Patent No.: US 9,468,644 B2
(45) Date of Patent: Oct. 18, 2016

(54) AQUEOUS COMPOSITIONS

(71) Applicant: Symrise AG, Holzminden (DE)

(72) Inventor: Cecile Kalem, Issy-les-Moulineuaux (FR)

(73) Assignee: Symrise AG, Holzminden (DE)

( * ) Notice: Subject to any disclaimer, the term of this patent is extended or adjusted under 35 U.S.C. 154(b) by 10 days.

(21) Appl. No.: 14/072,333

(22) Filed: Nov. 5, 2013

(65) Prior Publication Data
US 2014/0135349 A1    May 15, 2014

(30) Foreign Application Priority Data

Nov. 11, 2012   (EP) .................................... 12192147

(51) Int. Cl.
| | | |
|---|---|---|
| *A61K 31/522* | (2006.01) | |
| *A61K 8/42* | (2006.01) | |
| *A61K 31/137* | (2006.01) | |
| *A61K 31/192* | (2006.01) | |
| *A61K 31/4164* | (2006.01) | |
| *A61K 31/506* | (2006.01) | |
| *A61K 8/34* | (2006.01) | |
| *A61K 8/36* | (2006.01) | |
| *A61K 8/41* | (2006.01) | |
| *A61K 8/49* | (2006.01) | |
| *A61K 31/4418* | (2006.01) | |
| *A61Q 7/00* | (2006.01) | |
| *A61Q 19/00* | (2006.01) | |
| *A61K 8/04* | (2006.01) | |

(52) U.S. Cl.
CPC ............. *A61K 31/522* (2013.01); *A61K 8/042* (2013.01); *A61K 8/34* (2013.01); *A61K 8/345* (2013.01); *A61K 8/36* (2013.01); *A61K 8/41* (2013.01); *A61K 8/4926* (2013.01); *A61K 8/4946* (2013.01); *A61K 8/4953* (2013.01); *A61K 31/137* (2013.01); *A61K 31/192* (2013.01); *A61K 31/4164* (2013.01); *A61K 31/4418* (2013.01); *A61K 31/506* (2013.01); *A61Q 7/00* (2013.01); *A61Q 19/00* (2013.01)

(58) Field of Classification Search
None
See application file for complete search history.

(56) References Cited

U.S. PATENT DOCUMENTS

| | | | |
|---|---|---|---|
| 2009/0247529 A1* | 10/2009 | Lindahl et al. | 514/239.5 |
| 2010/0080761 A1 | 4/2010 | Herrmann | |
| 2010/0196504 A1 | 8/2010 | Schmaus et al. | |
| 2012/0156272 A1 | 6/2012 | Rebmann | |
| 2012/0157478 A1 | 6/2012 | Dawson, Jr. et al. | |
| 2012/0232152 A1 | 9/2012 | King-Smith et al. | |

FOREIGN PATENT DOCUMENTS

| | | |
|---|---|---|
| EP | 2286908 A2 | 2/2011 |
| WO | 2008/046796 A2 | 4/2008 |
| WO | WO2011047420 A1 * | 4/2011 |

OTHER PUBLICATIONS

Pillai et al: "1,2-Pentanedial—a Multifunctional Ingredient for Personal Care Applications," International Journal for Applied Science, 2005, pp. 12-22.

* cited by examiner

*Primary Examiner* — Wu-Cheng Winston Shen
*Assistant Examiner* — Taina D Matos Negron
(74) *Attorney, Agent, or Firm* — Dilworth & Barrese, LLP

(57) ABSTRACT

Suggested is a non-therapeutic aqueous composition for topical application, comprising
(a) at least one solid active agent having at 20° C. a solubility in water (20° dH) of less than 5 g/L;
(b) at least one 1,2-alkandiol having 4 to 12 carbon atoms; and
(c) at least one aliphatic alcohol having 2 to 4 carbon atoms.

12 Claims, No Drawings

AQUEOUS COMPOSITIONS

FIELD OF INVENTION

The present invention belongs to the area of cosmetic and pharmaceutical compositions and refers to compositions with improved solubility in water.

STATE OF THE ART

Actives for the treatment of dermatoses, in particular mycoses, and pain conditions form a manageable group of actives all of them having limitations with respect to their solubility in water. On one hand poor solubility makes it difficult to incorporate the actives into a stable ready-to-use composition, on the other hand compositions based on conventional cosmetically and pharmaceutically acceptable solvents or solvent compositions avoid liberation of the actives from the crèmes or capsules and decrease their bioavailability, both with respect to topical administration and oral uptake.

Typically, actives like for example minoxidil or ibuprofen are dissolved in ternary mixtures of ethanol, propylene glycol and water, however, for preparing for example a 5% b.w. solution of minoxidil that is stable for at least a number of days a mixture of 35% b.w. ethanol, 50% b.w. propylene glycol and 10% b.w. water is required. The high amount of organic needed to keep the solution stable is expensive and disadvantageous, in particular with respect to incorporation of the mixtures into final customer compositions, like a gel or an ointment.

International patent application WO 2012 040342 A1 (Conrex) claims a non-irritant composition useful in restoring hair comprising a solid, water-insoluble hair restorer, a dermal penetration facilitator and a solvent, said solvent being pentylene glycol or a mixture of pentylene glycol and propylene glycol.

Therefore, the problem underlying the present invention has been to develop improved solvent compositions for actives, preferably for actives from the group of anti-mycotica and pain relief agents in particular of the so-called NSAID type—said actives exhibiting very poor solubility in water. Compared to solvent compositions known from the state of the art the new alternatives should provide the possibility either to dissolve more active in the same amount of solvent or to decrease the amount of organic solvent uptake while dissolving the same amount of active. The invention also addresses the problem of keeping the compositions stable and avoiding phase separation or sedimentation after longer storage times or higher or lower storage temperatures (for example 5 or 40° C.). Finally, the solvents should also support liberation of the actives from a cosmetic or pharmaceutical composition in order to shorten the release time and to improve bioavailability of the compounds.

DESCRIPTION OF THE INVENTION

Object of the present invention is a non-therapeutic aqueous composition for topical application, comprising (a) at least one solid active agent having at 20° C. a solubility in water (20° $dH^1$) of less than 5 g/L;

[1] "dH" stands for "Deutsche Härte" providing information about the amount of Ca and MF ions in the water.

(b) at least one 1,2-alkandiol having 4 to 12 carbon atoms; and (c) at least one aliphatic alcohol having 2 to 4 carbon atoms.

Surprisingly, it has been observed, that ternary mixtures of lower 1,2-alkandiols, aliphatic alcohols and water represent powerful solvents for a huge number of actives for cosmetics and pharmaceuticals showing usually a very poor solubility in water. Compared to the state of the art, the new compositions allow decreasing the amount of organic solvent in the final products while dissolving the same amount of active. The compositions also show improved storage stability, both at high and low temperatures. Finally, the mixtures improve liberation of the actives out of their compositions and thus improve their biological availability both via topical applications or oral uptake.

Active Agents

Active agents with poor water solubility falling under the present invention encompass in particular anti-mycotica and pain relief agents, and more particularly the group consisting of minoxidil, erythromycin, dimetindene, beta methasone, ibuprofen, ketoprofene, diclofenac, metronidazole, acyclovir, imiquimod, terbinafine, docosanol, cyclopyroxolamine, and their mixtures:

Minoxidil (6-piperidin-1-ylpyrimidine-2,4-diamine 3-oxide) is an antihypertensive vasodilator medication which also slows or stops hair loss and promotes hair regrowth.

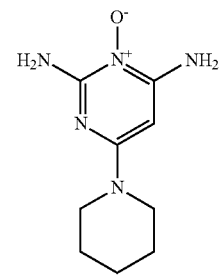 [SMILES: Nc1cc(N2CCCCC2)nc(N)[n+]1[O-]]

Now off-patent, it is available over-the-counter for the treatment of androgenic alopecia. Minoxidil must be used indefinitely for continued support of existing hair follicles and the maintenance of any experienced hair regrowth. It is marketed under many trade names, including Rogaine/Regaine, Vanarex, Mintop and Loniten (oral), and Avacor Physician's Formulation. Kopexil is a derivative of minoxidil missing the piperidine substituent; see also U.S. Pat. No. 3,644,364 (Upjohn).

Erythromycin is a macrolide antibiotic that has an antimicrobial spectrum similar to or slightly wider than that of penicillin, and is often used for people who have an allergy to penicillin.

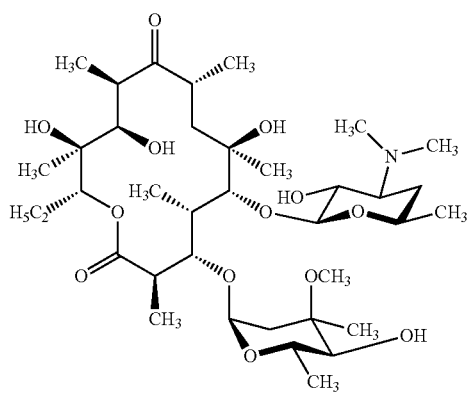

Recent studies have also shown that it can be used as a mild anti-depressant. For respiratory tract infections, it has better coverage of atypical organisms, including *Mycoplasma* and legionellosis. It was first marketed by Eli Lilly and Company, and it is today commonly known as EES (erythromycin ethylsuccinate, an ester prodrug that is commonly administered). In structure, this macrocyclic compound contains a 14-membered lactone ring with ten asymmetric centres and two sugars (L-cladinose and D-desosamine), making it a compound very difficult to produce via synthetic methods. Erythromycin is produced from a strain of the actinomycete *Saccharopolyspora erythraea* (see U.S. Pat. No. 2,653,899—Eli Lily).

Dimetindene, also known as Fenistil (RS-dimethyl(2-(3-[pyridin-2-yl)ethyl]-1H-inden-2-yl)ethyl)amine) is an antihistamine/anticholinergic used orally and locally as an antipruritic.

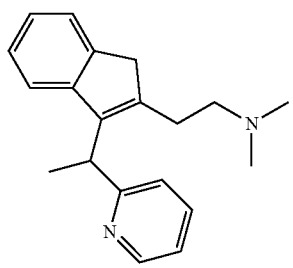 [SMILES: CC(C1=C(CCN(C)C)Cc2ccccc21)c1ccccn1]

Betamethasone (8S,9R,10S.11S,13S,14S,16S,17R)-9-fluoro-11,17-(2-hydroxyacetyl)-10,13,16-trimethyl-6,7,8,9,10,11,12,13,14,15,16,17-dodecahydro-3H-cyclopenta(alpha)phenanthren-3-one) is a potent glucocorticoid steroid with anti-inflammatory and immunosuppressive properties.

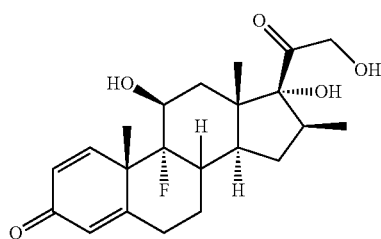

Unlike other drugs with these effects, betamethasone does not cause water retention. It is applied as a topical cream, ointment, foam, lotion or gel to treat itching. Betamethasone sodium phosphate is sometimes prescribed as an intramuscular injection (I.M) for itching from various ailments, including allergic reactions to poison ivy and similar plants (see U.S. Pat. No. 3,053,865—Merck).

Ibuprofen (RS)-2-(4-(2-methylpropyl)phenyl)propanoic acid) from the nomenclature isobutyl-propanoic-phenolic acid) is a non-steroidal anti-inflammatory drug (NSAID) used for relief of symptoms of arthritis, fever, as an analgesic (pain reliever), especially where there is an inflammatory component, and dysmenorrhea.

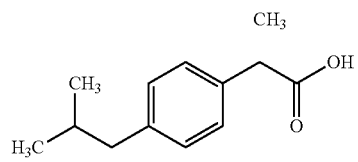

Ibuprofen is known to have an antiplatelet effect, though it is relatively mild and somewhat short-lived when compared with aspirin or other better-known antiplatelet drugs. In general, ibuprofen also acts as a vasoconstrictor, having been shown to constrict coronary arteries and some other blood vessels mainly because it inhibits the vasodilating prostacyclin produced by cyclooxygenase 2 enzymes. Ibuprofen was derived from propanoic acid by the research arm of Boots Group during the 1960s and was patented in 1961. Originally marketed as Brufen, ibuprofen is available under a variety of popular trademarks, including Motrin, Nurofen, Advil, and Nuprin (see U.S. Pat. No. 3,385,886—Boots).

Ketoprofen (RS)2-(3-benzoylphenyl)-propionic acid is another one of the propionic acid class of non-steroidal anti-inflammatory drug (NSAID) with analgesic and antipyretic effects.

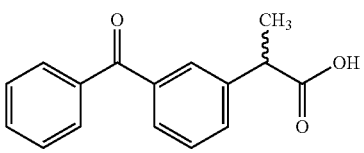 [SMILES: CC(C(=O)O)c1cccc(C(=O)c2ccccc2)c1]

It acts by inhibiting the body's production of prostaglandins (see U.S. Pat. No. 3,641,127—Rhone-Poulenc).

Diclofenac is also a non-steroidal anti-inflammatory drug (NSAID) taken to reduce inflammation and as an analgesic reducing pain in certain conditions.

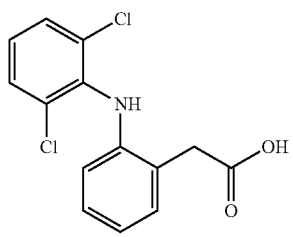 [SMILES: O=C(O)Cc1ccccc1Nc1c(Cl)cccc1Cl]

The name is derived from its chemical name: 2-(2,6-dichloranilino) phenylacetic acid. In the United Kingdom, India, Brazil and the United States, it may be supplied as either the sodium or potassium salt, in China most often as the sodium salt, while in some other countries only as the potassium salt. Diclofenac is available as a generic drug in a number of formulations. Over-the-counter (OTC) use is approved in some countries for minor aches and pains and fever associated with common infections (see U.S. Pat. No. 3,558,690—Ciba-Geigy).

Metronidazole (2-(2-methyl-5-nitro-1H-imidazol-1-yl) ethanol) is a nitroimidazole antibiotic medication used particularly for anaerobic bacteria and protozoa.

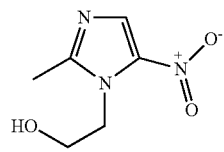

Metronidazole is an antibiotic, amebicide, and antiprotozoal. It is the drug of choice for first episodes of mild-to-moderate *Clostridium difficile* infection. It is marketed in the U.S.A. by Pfizer and globally by Sanofiunder the trade name Flagyl, in Pakistan and Bangladesh also as Nidagyl by Star Laboratories, and in Thailand, as Mepagyl by Thai Nakhorn Patana. It is also marketed in UK by Milpharm Limited and Almus Pharmaceuticals. Metronidazole was developed in 1960. Metronidazole is used also as a gel preparation in the treatment of the dermatological conditions such as rosaceae and fungating tumours (see U.S. Pat. No. 2,944,061—Rhone Poulenc).

Acyclovir or acyclovir (USAN, former BAN), chemical name acycloguanosine (2-Amino-1,9-dihydro-9-((2-hydroxyethoxy)methyl)-6H-Purin-6-one), abbreviated as ACV is a guanosine analogue antiviral drug, marketed under trade names such as Cyclovir, Herpex, Acivir, Acivirax, Zovirax, and Xovir. The solid active agent has a solubility in water (20° dH) at 20° C. of less than 5 g/L.

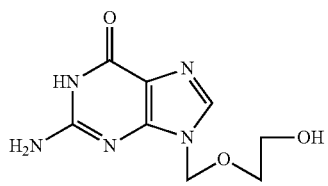

One of the most commonly used antiviral drugs; it is primarily used for the treatment of herpes simplex virus infections, as well as in the treatment of *varicella zoster* (chickenpox) and herpes zoster (shingles); see also U.S. Pat. No. 4,199,574 (Wellcome).

Imiquimod (3-(2-methylpropyl)-3,5,8-triazatricyclo[7.4.0.0.$^{2,6}$]trideca-1(9),2(6),4,7,10,12-hexaen-7-amine, INN) is a prescription medication that acts as an immune response modifier.

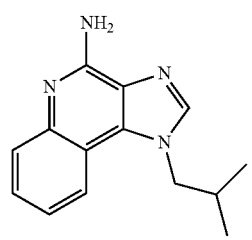 [SMILES: CC(C)Cn1cnc2c(N)nc3ccccc3c21]

It is marketed by Meda AB, Graceway Pharmaceuticals and iNova Pharmaceuticals under the trade names Aldara and Zyclara, and by Mochida as Beselna. It is also referred to as R-837 (see U.S. Pat. No. 4,689,338—Riker).

Terbinafine, more particularly terbinafine hydrochloride [(2E)-6,6-dimethylhept-2-en-4-yn-1-yl](methyl)(naphthalen-1-ylmethyl)amine) is a synthetic allylamine antifungal from Novartis. It is highly lipophilic in nature and tends to accumulate in skin, nails, and fatty tissues.

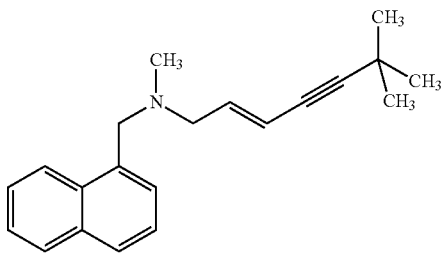 [SMILES: CN(C/C=C/C#CC(C)(C)C)Cc1cccc2ccccc12]

It is sold by the name Lamisil in Argentina, Australia, Belgium, Brazil, Canada, Chile, Egypt, Finland, France, Germany, Greece, Hungary, Iceland, Ireland, Israel, Mexico, Pakistan, Peru, New Zealand, Norway, Romania, Russia, Slovenia, South Africa, Sweden, United Kingdom, United States and Venezuela, also sold under the name Corbinal andTerbisil in Turkey and under the name "undofen cream" in Poland. As a generic it is sold under the name Zabel in Australia. It is also available as a generic medication in the United States, United Kingdom, Belgium, Switzerland and Brazil. In India, Terbinafine hydrochloride is available in topical form under the brand name Sebifin (Ranbaxy Labs), Zimig (GSK Pharma) and mycoCeaze (Progres̀ Laboratories). MycoVa, developed by Apricus Biosciences, is a topical nail solution of terbinafine and DDAIP which has completed three Phase III studies for the treatment of onychomycosis (see U.S. Pat. No. 4,755,534—Sandoz)

Docosanol, also known as behenyl alcohol, is a saturated fatty alcohol used traditionally as an emollient, emulsifier, and thickener in cosmetics, nutritional supplement (as an individual entity and also as a constituent of policosanol), and more recently, in a Food and Drug Administration (FDA) approved pharmaceutical, Abreva, approved as an antiviral agent for reducing the duration of cold sores caused by the herpes simplex virus.

Ciclopiroxolamine (6-cyclohexyl-1-hydroxy-4-methylpyridin-2(1H)-one) also called Batrafen, Loprox, Mycoster, Penlac and Stieprox, is a synthetic antifungal agent for topical dermatologic treatment of superficial mycoses.

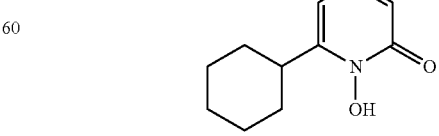

It is most useful against *Tinea versicolor* (see U.S. Pat. No. 3,883,545—Marck).

Solvents

The solvents according to the present invention represent ternary mixtures of certain 1,2-alkandiols, certain aliphatic alcohols and water.

(i) 1,2-Alkandiols. Suitable 1,2-alkandiols encompass 1,2-butadiol, 1,2-pentandiol, 1,2-hexandiol,1,2-heptanddiol, 1,2-octandiol, 1,2-nonandiol, 1,2-decandiol, 1,2-undecandiol, 1,2,dodecandiol and their mixtures. The preferred 1,2-alkandiol is 1,2-pentandiol.

(ii) Aliphatic alcohols. Suitable aliphatic alcohols are selected from the group consisting of ethanol, n-propanol, isopropylalcohol, the isomeric butanols and their mixtures. The preferred species is ethanol, in particular with a purity of at least 95%.

Overall preferred are solvent mixtures wherein the 1,2-alkandiol is 1,2-pentandiol and the aliphatic alcohol is ethanol.

Non-Therapeutic Compositions

More particularly, the invention refers to a non-therapeutic composition, comprising (a) about 1.0 to about 10.0% b.w., preferably about 2.0 to about 8.0% b.w. and more preferably about 2.5 to about 5.0% b.w. of at least one solid active agent having at 20° C. a solubility in water (20° dH) of less than 5 g/L, (b) about 15 to about 50% b.w., preferably about 20 to about 40% b.w. and more preferably about 25 to about 35% b.w. of at least 1,2-alkandiol having 4 to 12 carbon atoms; and;

(c) about 15 to about 25% b.w., preferably about 20 to about 22% b.w. of at least one aliphatic alcohol having 2 to 4 carbon atoms, on condition that the amounts add with water to give 100% b.w. Preferably, the amount of water in the compositions is of from about 10 to about 50% b.w., preferably from about 15 to about 40% b.w. and more preferably from about 25 to about 35% b.w.

Pharmaceutical Compositions

In a second embodiment the invention also encompasses a pharmaceutical composition, comprising (a) at least one solid active agent having at 20° C. a solubility in water (20° dH) of less than 5 g/L;

(b) at least one 1,2-alkandiol having 4 to 12 carbon atoms; and (c) at least one aliphatic alcohol having 2 to 4 carbon atoms for the treatment of dermatologic diseases or pain.

Said compositions may comprise active agents which selected from the group consisting of minoxidil, erythromycin, dimetindene, betamethasone, ibuprofen, ketoprofen, diclofenac, metronidazole, acyclovir, imiquimod, terbinafine, docosanol, cyclopyroxolamine, and their mixtures.

As 1,2-alkandiol the compositions may comprise 1,2-butadiol, 1,2-pentandiol, 1,2-hexandiol, 1,2-heptanddiol, 1,2-octandiol, 1,2-nonandiol, 1,2-decandiol, 1,2-undecandiol, 1,2,dodecandiol or their mixtures. The aliphatic alcohols are selected from ethanol, n-propanol, isopropylalcohol, the isomeric butanols and their mixtures. Preferred are aqueous mixtures of 1,2-pentandiol and ethanol.

More particularly, the pharmaceutical compositions comprise (a) about 1.0 to about 10.0% b.w., preferably about 2.0 to about 8.0% b.w. and more preferably about 2.5 to about 5.0% b.w. of at least one solid active agent having at 20° C. a solubility in water (20° dH) of less than 5 g/L, (b) about 15 to about 50% b.w., preferably about 20 to about 40% b.w. and more preferably about 25 to about 35% b.w. of at least 1,2-alkandiol having 4 to 12 carbon atoms; and;

(c) about 15 to about 25% b.w., preferably about 20 to about 22% b.w. of at least one aliphatic alcohol having 2 to 4 carbon atoms, on condition that the amounts add with water to give 100%. Preferably, the amount of water in the compositions is of from about 10 to about 50% b.w., preferably from about 15 to about 40% b.w. and more preferably from about 25 to about 35% b.w.

The compositions are suitable for topical or oral application. They may represent a cream, a gel, a lotion, an ointment, a powder, a tablet, or a capsule.

Industrial Application

The invention also covers a method for improving the solubility of a solid in water, the improvement wherein a solid that is selected from the group consisting of minoxidil, erythromycin, dimetindene, betamethasone, ibuprofen, ketoprofen, diclofenac, metronidazole, acyclovir, imiquimod, terbinafine, docosanol, cyclopyroxolamine, and their mixtures, is dissolved in water in the presence of a solubilizing amount of a mixture consisting of an 1,2-alkandiol having 4 to 12 carbon atoms and an aliphatic alcohol having 2 to 4 carbon atoms.

Finally, the invention refers to a mixture comprising (a) at least one 1,2-Alkandiol having 4 to 12 carbon atoms, (b) at least one aliphatic alcohol having 2 to 4 carbon atoms, and (c) water as a solvent for solids selected from the group consisting of minoxidil, erythromycin, dimetindene, betamethasone, ibuprofen, ketoprofen, diclofenac, metronidazole, acyclovir, imiquimod, terbinafine, docosanol, cycclopyroxolamine, and their mixtures.

EXAMPLES

Examples 1 to 7

Comparative Examples C1 to C5

5 g Minoxidil and an aqueous mixture of
(a) ethanol and 1,2-pentandiol and
(b) ethanol and propylene glycol
were stirred for 1 minute. The solutions were placed in clear glass bottles and stored at 2, 20 and 40° C. for 11 days. The aspects of the mixtures are described in the following Tables 1 and 2. The classification means: (+)=clear, no precipitation, (#) opaque and (−) precipitation. Examples 1 to 7 are according to the invention, examples C1 to C5 serve for comparison.

TABLE 1

Solubility of Minoxidil over a storage time of 11 days

| Composition | 1 | 2 | 3 | 4 | 5 | 6 | 7 | C1 | C2 | C3 | C4 | C5 |
| --- | --- | --- | --- | --- | --- | --- | --- | --- | --- | --- | --- | --- |
| Ethanol 96° | 25 | 20 | 25 | 20 | 25 | 20 | 25 | 25 | 30 | 25 | 30 | 25 |
| 1,2-pentanediol | 15 | 20 | 20 | 25 | 25 | 30 | 30 | — | — | — | — | — |
| Propylene glycol | — | — | — | — | — | — | — | 35 | 35 | 40 | 40 | 50 |
| Minoxidil EU PH | 5 | 5 | 5 | 5 | 5 | 5 | 5 | 5 | 5 | 5 | 5 | 5 |
| Water | | | | | | | ad 100 | | | | | |
| Solubility/optical aspect | | | | | | | | | | | | |
| at 2° C. | # | # | # | # | # | # | # | − | − | − | − | − |
| at 20° C. | # | # | # | # | + | + | + | − | − | − | − | − |
| at 40° C. | + | + | + | + | + | + | + | + | + | + | + | + |

The results show that aqueous compositions comprising a mixture of ethanol and 1,2-pentandiol allow to dissolve the active both at low and high temperatures with a lower amount of organic solvent compared to the mixture based on ethanol and propylene glycol.

Examples 8 to 14

Comparative Examples C6 to C10

The examples presented above were repeated, but the compositions stored under the same temperature conditions for 18 days. The results are presented in Table 2. Examples 8 to 14 are according to the invention, examples C6 to C10 serve for comparison.

TABLE 2

Solubility of minoxidil over a storage time of 18 days

| Composition | 8 | 9 | 10 | 11 | 12 | 13 | 14 | C6 | C7 | C8 | C9 | C10 |
|---|---|---|---|---|---|---|---|---|---|---|---|---|
| Ethanol 96° | 25 | 30 | 25 | 30 | 25 | 30 | 35 | 25 | 30 | 25 | 30 | 35 |
| 1,2-pentanediol | 35 | 35 | 40 | 40 | 45 | 45 | 50 | — | — | — | — | — |
| Propylene glycol | — | — | — | — | — | — | — | 35 | 35 | 40 | 40 | 50 |
| Minoxidil EU PH | 5 | 5 | 5 | 5 | 5 | 5 | 5 | 5 | 5 | 5 | 5 | 5 |
| Water | ad 100 | | | | | | | | | | | |
| Solubility/optical aspect | | | | | | | | | | | | |
| at 2° C. | + | + | + | + | + | + | + | − | − | − | − | # |
| at 20° C. | + | + | + | + | + | + | + | # | # | # | # | + |
| at 40° C. | + | + | + | + | + | + | + | + | + | + | + | + |

Again, the results show that in case of the mixture of ethanol/1,2-propandiol less organic solvent is necessary to dissolve the active over the full temperature spectrum.

Examples 15 to 21

Comparative Examples C11 to C15

7 g Acyclovir and an aqueous mixture of
(a) ethanol and 1,2-hexandiol and
(b) ethanol and propylene glycol
were stirred for 1 minute and stored under the same conditions as described above. Examples 15 to 21 are according to the invention, examples C11 to C15 serve for comparison.

TABLE 3

Solubility of Acyclovir over a storage time of 18 days

| Composition | 15 | 16 | 17 | 18 | 19 | 20 | 21 | C11 | C12 | C13 | C14 | C15 |
|---|---|---|---|---|---|---|---|---|---|---|---|---|
| Ethanol 96° | 25 | 20 | 25 | 20 | 25 | 20 | 25 | 25 | 30 | 25 | 30 | 25 |
| 1,2-pentanediol | 15 | 20 | 20 | 25 | 25 | 30 | 30 | — | — | — | — | — |
| Propylene glycol | — | — | — | — | — | — | — | 35 | 35 | 40 | 40 | 50 |
| Acyclovir | 7 | 7 | 7 | 7 | 7 | 7 | 7 | 7 | 7 | 7 | 7 | 7 |
| Water | ad 100 | | | | | | | | | | | |
| Solubility/optical aspect | | | | | | | | | | | | |
| at 2° C. | + | + | + | + | + | + | + | # | # | # | # | # |
| at 20° C. | + | + | + | + | + | + | + | # | # | # | # | # |
| at 40° C. | + | + | + | + | + | + | + | + | + | + | + | + |

Examples 22 to 28

Comparative Examples C16 to C20

4 g Ibuprofen and an aqueous mixture of
(a) n-propanol and 1,2-decandiol and
(b) n-propanol and propylene glycol
were stirred for 1 minute and stored under the same conditions as described above. Examples 22 to 28 in Table 4 are according to the invention, examples C16 to C20 serve for comparison.

TABLE 4

Solubility of Ibuprofen over a storage time of 18 days

| Composition | 22 | 23 | 24 | 25 | 26 | 27 | 28 | C16 | C17 | C18 | C19 | C20 |
|---|---|---|---|---|---|---|---|---|---|---|---|---|
| n-Propanol | 25 | 20 | 25 | 20 | 25 | 20 | 25 | 25 | 30 | 25 | 30 | 25 |
| 1,2-decandiol | 15 | 20 | 20 | 25 | 25 | 30 | 30 | — | — | — | — | — |
| Propylene glycol | — | — | — | — | — | — | — | 35 | 35 | 40 | 40 | 50 |
| Ibuprofen | 4 | 4 | 4 | 4 | 4 | 4 | 4 | 4 | 4 | 4 | 4 | 4 |
| Water | ad 100 | | | | | | | | | | | |
| Solubility/optical aspect | | | | | | | | | | | | |
| at 2° C. | + | + | + | + | + | + | + | # | # | # | # | # |
| at 20° C. | + | + | + | + | + | + | + | # | # | # | + | + |
| at 40° C. | + | + | + | + | + | + | + | + | + | + | + | + |

Examples 29 to 35

Comparative Examples C21 to C25

8 g Metronidazol and an aqueous mixture of
(a) n-butanol and 1,2-dodecandiol and
(b) n-butanol and butylene glycol
were stirred for 1 minute and stored under the same conditions as described above. Examples 29 to 35 in Table 5 are according to the invention, examples C21 to C25 serve for comparison.

TABLE 5

Solubility of Metronidazol over a storage time of 18 days

| Composition | 29 | 30 | 31 | 32 | 33 | 34 | 35 | C21 | C22 | C23 | C24 | C25 |
|---|---|---|---|---|---|---|---|---|---|---|---|---|
| n-Butanol | 25 | 20 | 25 | 20 | 25 | 20 | 25 | 25 | 30 | 25 | 30 | 25 |
| 1,2-dodecandiol | 15 | 20 | 20 | 25 | 25 | 30 | 30 | — | — | — | — | — |
| Butylene glycol | — | — | — | — | — | — | — | 35 | 35 | 40 | 40 | 50 |
| Metronidazol | 8 | 8 | 8 | 8 | 8 | 8 | 8 | 8 | 8 | 8 | 8 | 8 |
| Water | ad 100 | | | | | | | | | | | |
| Solubility/optical aspect | | | | | | | | | | | | |
| at 2° C. | # | # | # | # | # | # | # | − | − | − | − | − |
| at 20° C. | # | # | # | # | # | # | # | # | # | # | + | + |
| at 40° C. | + | + | + | + | + | + | + | # | # | # | # | # |

Examples 36 and 37

3 gels comprising the active Terbinafine (HCl) were prepared, one without 1,2-pentadiol and the two other comprising 5 and 10% 1,2-pentandiol respectively. 5 mg of each gel were extracted under vigorous shaking using ethanol/water (50:50 w/v) as the solvent. The liberation of the active was followed over a period of 60 minutes by taking samples and determining the amount of active by HPLC against a calibrated standard. The compositions of the gels and the liberation results are provided in Table 6. The results clearly show that adding of 1,2-pendiol shortens the period for liberating the active from the gel.

TABLE 6

Liberation of Terbinafine (HCl) from a gel (amounts in % b.w.)

| Compound | Control | 36 | 37 |
|---|---|---|---|
| Terbinafine (HCl) | 1.0 | 1.0 | 1.0 |
| Ethanol | 40.0 | 40.0 | 40.0 |
| Propylenglycol | 5.0 | 5.0 | 5.0 |
| Polysorbat 80 | 1.5 | 1.5 | 1.5 |
| Metocel E4N | 2.7 | 2.7 | 2.7 |
| 1,2-Pentandiol | — | 5.0 | 10.0 |
| Water | | ad 100 | |
| Liberation of Terbinafin (HCl) after | | | |
| 10 minutes | 60 | 75 | 83 |
| 30 minutes | 65 | 83 | 85 |
| 60 minutes | 79 | 90 | 90 |

Examples 38 and 39

3 gels comprising the active Ciclopiroxolamine were prepared, one without 1,2-pentadiol and the two other comprising 5 and 10% 1,2-pentandiol respectively. 5 mg of each gel were extracted under vigorous shaking using ethanol/water (50:50 w/v) as the solvent. The liberation of the active was followed over a period of 60 minutes by taking samples and determining the amount of active by HPLC against a calibrated standard. The compositions of the gels and the liberation results are provided in Table 7. The results clearly show that adding of 1,2-pendiol shortens the period for liberating the active from the gel.

TABLE 7

Liberation of Ciclopiroxolamine from a gel (amounts in % b.w.)

| Compound | Control | 38 | 39 |
|---|---|---|---|
| Ciclopiroxolamine | 1.0 | 1.0 | 1.0 |
| Ethanol | 30.0 | 30.0 | 30.0 |
| Metocel E4N | 2.7 | 2.7 | 2.7 |
| 1,2-Pentandiol | — | 5.0 | 10.0 |
| Water | | ad 100 | |
| Liberation of ciclopiroxolamine after | | | |
| 10 minutes | 70 | 79 | 81 |
| 30 minutes | 80 | 84 | 85 |
| 60 minutes | 85 | 87 | 88 |

The invention claimed is:

1. An aqueous composition for topical application, comprising
    (a) at least one solid active agent having at 20° C. a solubility in water, 20° dH, of less than 5 g/L selected from the group consisting of minoxidil, erythromycin, dimetindene, betamethasone, ibuprofen, ketoprofen, diclofenac, metronidazole, acyclovir, imiquimod, docosanol and mixtures thereof; and
    a solvent comprising a mixture of
    (b) at least one 1,2-alkandiol having 4 to 12 carbon atoms; and
    (c) at least one aliphatic alcohol having 2 to 4 carbon atoms.

2. The composition of claim 1, wherein the 1,2-alkandiol is selected from the group consisting of 1,2-butadiol, 1,2-pentandiol, 1,2-hexandiol, 1,2-heptandiol, 1,2-octandiol, 1,2-nonandiol, 1,2-decandiol, 1,2-undecandiol, 1,2-dodecandiol and mixtures thereof.

3. The composition of claim 1, wherein the aliphatic alcohol is selected from the group consisting of ethanol, n-propanol, isopropylalcohol, one of the isomeric butanols and mixtures thereof.

4. The composition of claim 1, wherein the 1,2-alkandiol is 1,2-pentandiol and the aliphatic alcohol is ethanol.

5. The composition of claim 1, comprising
(a) about 1.0 to about 10.0% by weight of at least one solid active agent having at 20° C. a solubility in water (20° dH) of less than 5 g/L selected from the group consisting of minoxidil, erythromycin, dimetindene, betamethasone, ibuprofen, ketoprofen, diclofenac, metronidazole, acyclovir, imiquimod, docosanol and mixtures thereof,
(b) about 15 to about 50% by weight of at least 1,2-alkandiol having 4 to 12 carbon atoms; and;
(c) about 15 to about 25% by weight of at least one aliphatic alcohol having 2 to 4 carbon atoms, on condition that the amounts add with water to give 100% by weight.

6. A composition comprising
(a) at least one solid active agent having at 20° C. a solubility in water (20° dH) of less than 5 g/L, selected from the group consisting of minoxidil, erythromycin, dimetindene, betamethasone, ibuprofen, ketoprofen, diclofenac, metronidazole, acyclovir, imiquimod, docosanol and mixtures thereof;
(b) at least one 1,2-alkandiol having 4 to 12 carbon atoms; and
(c) at least one aliphatic alcohol having 2 to 4 carbon atoms for the treatment of dermatologic diseases or pain.

7. The composition of claim 6, wherein the 1,2-alkandiol is selected from the group consisting of 1,2-butadiol, 1,2-pentandiol, 1,2-hexandiol, 1,2-heptandiol, 1,2-octandiol, 1,2-nonandiol, 1,2-decandiol, 1,2-undecandiol, 1,2,dodecandiol and mixtures thereof.

8. The composition of claim 6, wherein the aliphatic alcohol is selected from the group consisting of ethanol, n-propanol, isopropylalcohol, one of the isomeric butanols and mixtures thereof.

9. The composition of claim 6, wherein the composition is for topical or oral application.

10. The composition of claim 6, wherein the composition is a cream, a gel, a lotion, an ointment, a powder, a tablet or a capsule.

11. A method for improving solubility of a solid active agent in water, comprising dissolving the solid active agent in water in the presence of a mixture of solvent consisting of an 1,2-alkandiol having 4 to 12 carbon atoms and an aliphatic alcohol having 2 to 4 carbons, wherein the solid active agent having at 20° C. solubility in water, 20° dH, of less than 5 g/L is selected from group consisting of minoxidil, erythromycin, dimetindene, betamethasone, ibuprofen, ketoprofen, diclofenac, metronidazole, acyclovir, imiquimod, docosanol and mixtures thereof.

12. An aqueous composition for topical application, comprising
(a) at least one solid agent having at 20° C. a solubility in water, 20° dH, of less than 5 g/L selected from the group consisting of minoxidil, ibuprofen, acyclovir, metronidazole, terbinafine, cyclopyroxolamine and mixtures thereof; and
a solvent comprising a mixture of
(b) 1,2-pentandiol; and
(c) ethanol.

* * * * *